(12) United States Patent
Takagi et al.

(10) Patent No.: US 7,031,424 B2
(45) Date of Patent: *Apr. 18, 2006

(54) CT APPARATUS, CT IMAGING METHOD AND METHOD OF PROVIDING SERVICE USING THE SAME

(75) Inventors: Tarou Takagi, Hitachi (JP); Hiroshi Kamimura, Hitachi (JP); Sadao Uchikawa, Tokai (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/152,371

(22) Filed: Jun. 15, 2005

(65) Prior Publication Data

US 2005/0243965 A1 Nov. 3, 2005

Related U.S. Application Data

(63) Continuation of application No. 10/622,648, filed on Jul. 21, 2003, now Pat. No. 6,909,768.

(30) Foreign Application Priority Data

Jul. 22, 2002 (JP) .............................. 2002-211905

(51) Int. Cl.
*G01N 23/00* (2006.01)
(52) U.S. Cl. ............................................ 378/4; 378/62
(58) Field of Classification Search .................... 378/4, 378/62, 205, 207, 20, 164; 600/426
See application file for complete search history.

(56) References Cited

U.S. PATENT DOCUMENTS 5,211,164 A 5/1993 Allen .......................... 600/426
6,909,768 B1* 6/2005 Takagi et al. ................... 378/4

FOREIGN PATENT DOCUMENTS

| GB | 2274964 | 8/1994 |
| GB | 2174880 | 11/1996 |
| JP | 2000-107161 | 4/2000 |
| JP | 2000-298106 | 10/2000 |

* cited by examiner

*Primary Examiner*—David V. Bruce
*Assistant Examiner*—Courtney Thomas
(74) *Attorney, Agent, or Firm*—Antonelli, Terry, Stout and Kraus, LLP.

(57) ABSTRACT

A CT imaging method and apparatus in which an object is to be imaged by the CT apparatus using an X-ray or radiation, and a tomographic image of the object is obtained, wherein the object includes a reference portion. The processing the tomographic image is processed and a relative positional relation between a reference coordinate system of the object and a coordinate system of the CT apparatus is obtained. The object is imaged by the CT apparatus, and based on the relative positional relation, a tomographic image of a desired position of the object is obtained.

6 Claims, 10 Drawing Sheets

FIG.12

CT APPARATUS, CT IMAGING METHOD AND METHOD OF PROVIDING SERVICE USING THE SAME

CROSS REFERENCE TO RELATED APPLICATION

This is a continuation application of U.S. Ser. No. 10/622,648, filed Jul. 21, 2003, now U.S. Pat. No. 6,909,768, the contents of which are incorporated herein by reference.

BACKGROUND OF THE INVENTION

The present invention relates to an industrial computed tomographic (CT) apparatus, a CT imaging method and a method of providing service using the same.

In industrial X-ray CT apparatuses it is common practice to place an object of concern on a turntable that rotates in a horizontal plane and take a horizontally sliced tomographic image. When an object is put on the turntable of the X-ray CT apparatus, the user selects reference planes (horizontal plane, vertical plane, etc.) and aligns a coordinate system of the object with that of the turntable by using a square and level. In inclining the object, the user makes an adjustment by inserting a wedge-like jig under the object.

An industrial X-ray CT apparatus with a setting device that allows an object to be set in different positions and directions is disclosed in JP-A-2000-298106.

In a medical X-ray CT apparatus, a method is described in JP-A-2000-107161 which involves imaging a patient body with markings on his or her body surface and side surfaces and determining a position of a legion as a relative position from the body surface markings.

With JP-A-2000-298106, although the installation of an object to be imaged is made easier for the user, the work for determining reference planes of the object is difficult to achieve.

The method of JP-A-2000-107161 can be applied to medical apparatus because the position of a human body attached with markings on its surface is fixed. However, in industrial apparatus the reference position (reference plane) changes from one object to another, so this method cannot be applied.

SUMMARY OF THE INVENTION

An object of the present invention is to provide a CT apparatus, a CT imaging method and a method of providing service using these, in which, even when objects with different reference planes are set on a turntable for imaging, the user can easily set the objects without requiring a process of determining reference planes of the objects.

The present invention determines a geometric feature (information representing a geometry) of a contact surface between a marker and an object to be imaged by using a tomographic image from a CT apparatus of the object attached with the marker on a reference plane; determines from the geometric feature a positional relation between a reference coordinate system of the object and a coordinate system of the CT apparatus; and obtains from the positional relation a tomographic image (bit-map data) of a desired portion of the object.

Other objects, features and advantages of the invention will become apparent from the following description of the embodiments of the invention taken in conjunction with the accompanying drawings.

DETAILED DESCRIPTION OF THE EMBODIMENTS

First Embodiment

Figure 1:
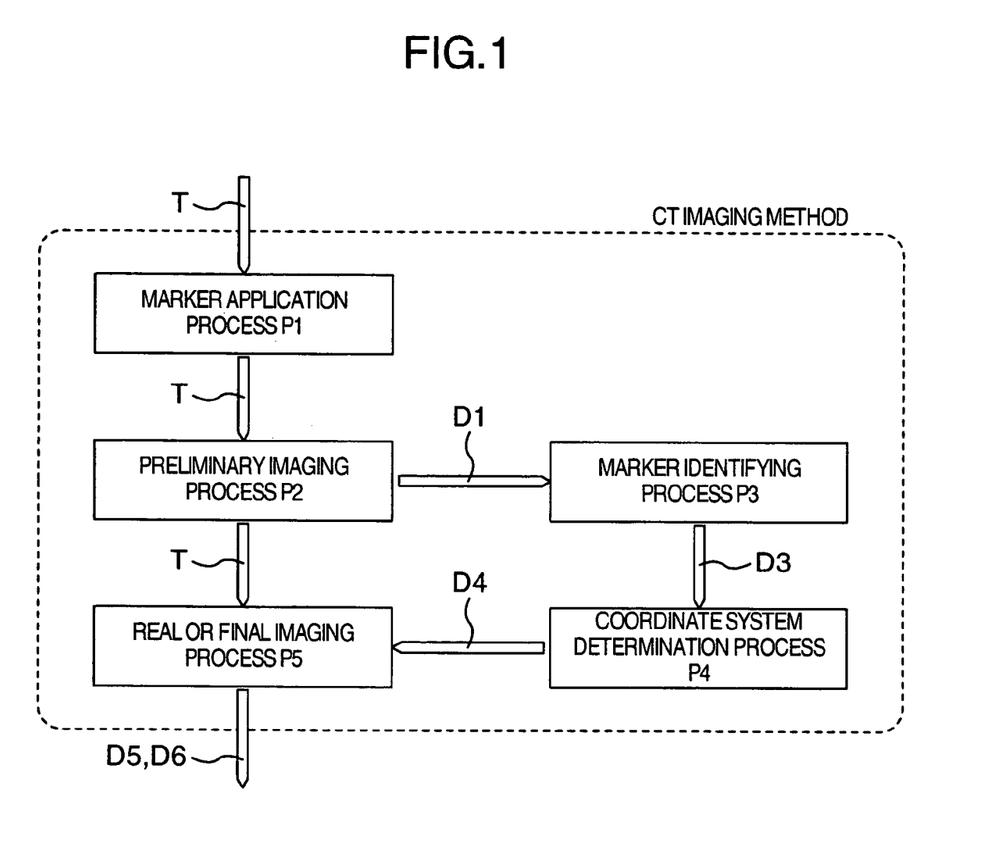
FIG. 1 is a diagram showing a first embodiment concerning a CT imaging method of the present invention.

A first embodiment of the present invention will be described by referring to the accompanying drawings. FIG. 1 illustrates a method of taking a CT image according to the first embodiment. This CT imaging method has a marker application process P1, a preliminary imaging process P2, a marker identifying process P3, a coordinate system determination process P4, and a full imaging process P5.

In the marker application process P1, a marker is attached to a reference plane of an object to be imaged T. For example, when the object has a plane as a horizontal or vertical reference, the marker is attached to that plane. If the object has a cylindrical plane as a horizontal or vertical reference, the marker is attached to that cylindrical plane. The marker is made of a material with an X-ray transmissivity (or attenuation rate) different from that of the object. For example, a material with a different density from that of the object has a different X-ray transmissivity. The marker size (length and width) is preferably in a range of 20 mm to 50 mm. The marker is also preferably made of a plastic material for easy bonding. The method of bonding the marker will be described later with reference to FIG. 2.

In the preliminary imaging process P2, the object T is placed on a turntable of an X-ray CT apparatus and is wholly imaged at intervals of five to 20 times of a target tomographic pitch. For example, if the target tomographic pitch (final desired tomographic pitch) is 0.4 mm, the image is performed at a greater interval of 2–8 mm.

Once the object is imaged by the X-ray CT apparatus, tomographic images (two-dimensional bit-map data) are produced for individual cross-sections. A number of tomographic images thus obtained are stacked together to produce a tomographic image set (three-dimensional bit-map data). In the preliminary imaging process P2, a coarse tomographic image set D1, a set of tomograms with a coarse (low) resolution, is obtained.

In the preliminary imaging process P2, to prevent the object from being shifted in position by the rotation of the turntable, the object need only be fixed and there is no necessity for adjusting a placement angle of the object. The construction of the X-ray CT apparatus used in P2 will be described by referring to FIG. 3.

In the marker identifying process P3, the coarse tomographic image set D1 obtained in the preliminary imaging process P2 is subjected to three-dimensional image processing to identify the marker. For example, if the object being imaged is made of aluminum, as in the case of an engine block, its density is about 2.7 g/cm$^3$. When a clay is used as the marker, its density is about 1.5 g/cm$^3$. In this case, the X-ray transmissivity of the marker is greater than that of the object and the X-ray attenuation rate of the marker is smaller than that of the object.

Since a density distribution in the interior of the object can be known by using the X-ray CT apparatus, it is possible to distinguish only the clay (marker) portion from the aluminum and air portions for its extraction. In this way, the marker is identified by taking advantage of these differences between the marker and the object in the density, X-ray transmissivity and X-ray attenuation rate.

The clay marker is plastically deformed when pressed against the surface of the object. When the surface of the object is flat, the marker's contact surface with the object is also flat. By performing plane extraction processing (processing to automatically recognize and extract a plane of more than a predetermined area) on this contact surface, geometric definitions (geometric features) of the contact surface can be calculated with the turntable as a reference. The geometric definitions of all contact surfaces thus calculated are recorded in a marker surface feature domain list D3. The plane extraction processing may employ a plane identification method described later, such as a surface domain expansion method. The marker identifying process P3 will be detailed by referring to FIG. 5.

In the coordinate system determination process P4, a coordinate system D4 of the object with the turntable taken as a reference is calculated from the geometric definitions of the contact surface between the marker and the object, which are recorded in the marker surface feature domain list D3. If a plurality of markers are all attached to planar surfaces, the individual contact surfaces are compared with a horizontal reference plane (XY plane) and vertical reference planes (YZ plane and ZX plane) with the turntable as a reference, and then an affine transformation matrix is determined which makes an overall angular difference minimum.

For example, the affine transformation matrix is determined so that a sum of the squares of angles between each marker and the reference planes is minimum. The affine transformation matrix is a matrix that represents a relation between two coordinate systems based on a linear combination of basic vectors. Here, matrices corresponding to a rotation and a translation of Cartesian coordinate systems are used. The detail of this process will be described with reference to FIG. 8.

In the real or final imaging process P5, the object T is imaged at a target tomographic pitch to produce high resolution tomographic images D5 and/or a tomographic image set D6, a final result of the process.

The tomographic images D5 and the tomographic image set D6 are bit-map data. The user (operator) inputs into the X-ray CT apparatus beforehand coordinate values of a portion the user wants to image. Since the coordinate system D4 of the object with the turntable taken as a reference is already calculated in the coordinate system determination process P4, the X-ray CT apparatus automatically corrects, before taking images, the coordinate values of the target portion entered using the coordinate system D4. This correction is made to determine the imaging position and the imaging range specified by the user in advance.

The X-ray CT apparatus also corrects the number of images. This correction is made, for example, when the imaging cross-sections are inclined to the horizontal plane as a result of performing the affine transformation on the imaging cross-sections specified by the user. The number of images to be taken is determined by dividing a length in the vertical direction of a domain from a lowest point to a highest point of the imaging cross-sections by a vertical resolution characteristic of the X-ray CT apparatus. In this way, based on the positional relation between the reference coordinate system of the object and the coordinate system of the X-ray CT apparatus, bit-map data of a desired portion of the object is obtained.

This CT imaging method has the above-described processes and thus can significantly automate the step of determining the coordinate systems D4 of objects to be imaged which have different (arbitrary) reference planes. That is, this method allows the user to omit the step of determining the reference planes of the objects, thus facilitating the installation of the objects and the operation of the X-ray CT apparatus.

Figure 2A:
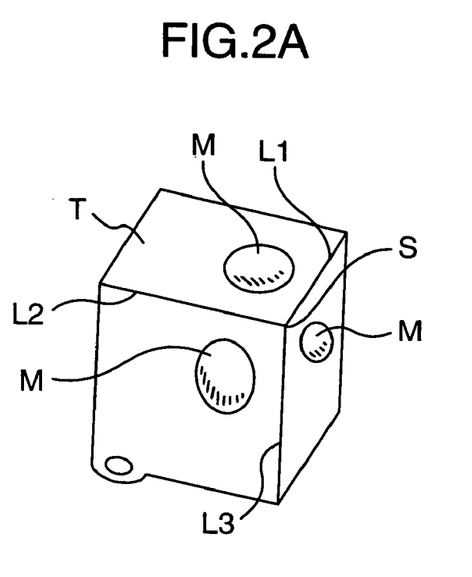
FIGS. 2A–2C are schematic diagrams showing a method of attaching markers to an object to be imaged, FIG. 2A representing an example of markers attached to three orthogonal planes, FIG. 2B representing an example of markers attached to a plane and a cylindrical surface, crossing each other at right angles, and FIG. 2C representing an example of markers attached to orthogonal two planes and one vertex.
Figure 2B:
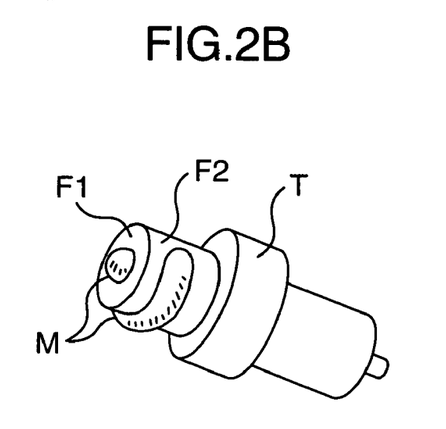
Figure 2C:
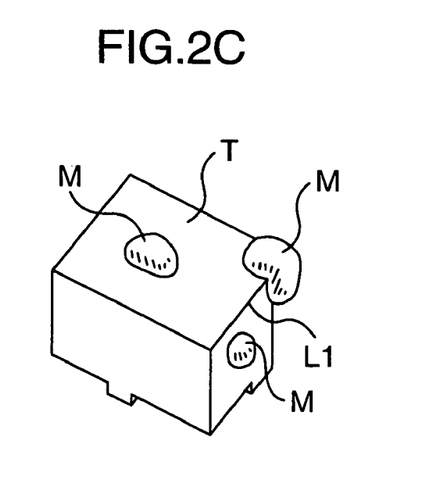

Examples of attaching markers to objects are schematically shown in FIG. 2A to FIG. 2C. There are different patterns of attaching the markers. These marker arrangement patterns are such as will allow the coordinate system determination process P4 to determine the affine transformation matrix.

FIG. 2A represents a case in which markers M are attached one to each of three orthogonal planes of an object T. In this case, an intersecting point S of the three planes constitutes a reference point of the coordinate system and intersecting lines L1–L3 between two planes constitute reference axes. In this example, all three markers M have different sizes. This allows the marker identifying process P3 to automatically identify individual markers M. For the purpose of distinguishing between the markers, the materials of the markers M may be differentiated.

FIG. 2B represents a case where markers M are bonded to a flat surface F1 and a cylindrical surface F2 of an object T, these planes intersecting each other at right angles. In this case, a center axis of the cylindrical surface F2 forms a reference axis of the coordinate system, and an intersecting point of the reference axis and the flat surface F1 constitutes a reference point of the coordinate system. With the surface domain expansion method described later, since a flat surface, cylindrical surface, spherical surface, revolution surface, quadratic surface and pushed or translated surface can be recognized and extracted, the coordinate system can be defined by using these surfaces. The revolution surface is a locus obtained by rotating a line (straight line, curved line, and a combination of these) about one straight line (center axis). The quadratic surface is a surface described by a quadratic equation of coordinate variables (X, Y, Z). The translated surface is a plane of locus obtained when a line is moved parallelly.

FIG. 2C represents a case where markers M are bonded to two orthogonal flat surfaces of an object T and to one vertex. In this case the vertex attached with the marker M constitutes a reference point of the coordinate system, and an intersecting line L1 between the two planes constitutes a reference axis. If the markers M are bonded to a vertex and an edge line of an object T, the contact surface between the markers M and the object T is not on one plane but on three or two divided planes. By identifying and extracting all of these contact surfaces in the marker identifying process P3 and determining an intersecting point and an intersecting line between them, it is possible to obtain geometric definitions of the vertex and edge line.

Figure 3:
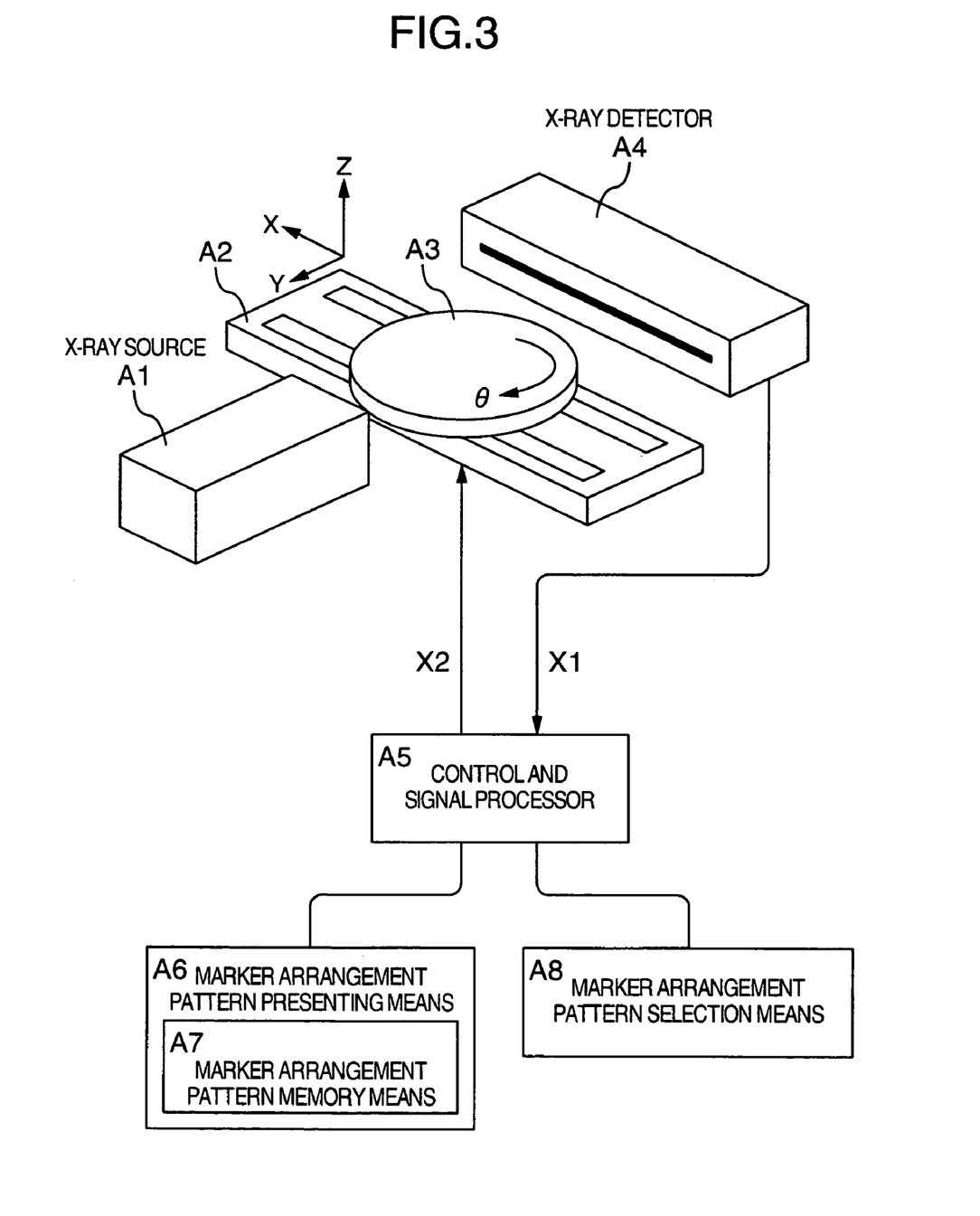
FIG. 3 is a schematic diagram showing an example of an X-ray CT apparatus of this invention.

Next, a construction of the X-ray CT apparatus used in the preliminary imaging process P2 is shown in FIG. 3. This X-ray CT apparatus has an X-ray source (radiation source) A1, a scanning mechanism A2, a turntable A3, an X-ray detector A4, a control and signal processor A5, a marker arrangement pattern presenting means A6, and a marker arrangement pattern selection means A8.

X-rays emitted from the X-ray source A1 penetrate an object (not shown) fixed on the turntable A3 and reach the X-ray detector A4 where they are converted into a detection signal X1. The detection signal X1 is sent from the X-ray detector A4 to the control and signal processor A5 where it is subjected to "reconstructive processing" to be converted into a tomographic image set (three-dimensional bit-map data).

The turntable A3 is rotated and translated by the scanning mechanism A2 according to a control signal X2 from the control and signal processor A5. The rotation is, for example, a movement in a direction of θ in FIG. 3. The translation includes, for example, a movement in an X direction of FIG. 3 (lateral direction or longitudinal direction) and a movement in a Z direction (vertical direction). By rotating or translating the turntable A3 with an object fixed on it, it is possible to radiate the X rays against the object from various directions and collect data (information) required for the reconstructive processing.

Unlike the conventional X-ray CT apparatus, the X-ray CT apparatus of this embodiment has the marker arrangement pattern presenting means A6 and the marker arrangement pattern selection means A8. The marker arrangement pattern presenting means A6 has a marker arrangement pattern memory means A7. The marker arrangement pattern memory means A7 stores a plurality of marker arrangement patterns in advance, such as shown in FIG. 2. The marker arrangement pattern presenting means A6 has a display means (not shown) such as a CRT display and displays a list of marker arrangement patterns on this display. The display means may also double as a display means used to control the X-ray CT apparatus.

Figure 4:
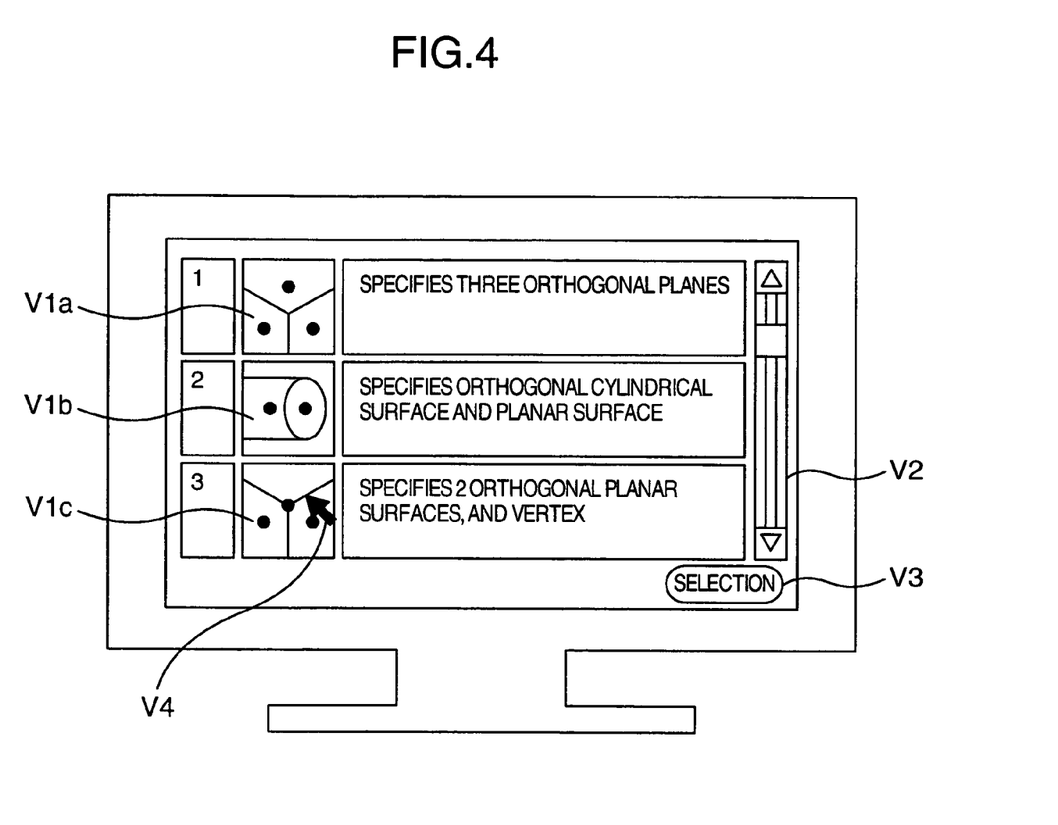
FIG. 4 is a diagram showing an example screen displayed on a marker arrangement pattern presenting means A6.

An example of screen the marker arrangement pattern presenting means A6 displays on the display means is shown in FIG. 4. On this screen are shown icons V1a–V1c, a scrollbar V2, a selection button V3, and a cursor (arrow cursor) V4. In FIG. 4, the icons V1a–V1c correspond to the marker arrangement patterns shown in FIG. 2A–FIG. 2C.

The marker arrangement pattern selection means A8 comprises a general input means such as mouse and keyboard. The user may move the cursor V4 on the screen using the mouse to drag the scrollbar V2 to display a desired marker arrangement pattern on the screen. Then, the user selects an icon corresponding to the desired marker arrangement pattern with the cursor V4 and then clicks on the selection button V3 to specify the desired marker arrangement pattern. The user can also specify a desired marker arrangement pattern by entering a number corresponding to the desired marker arrangement pattern from the keyboard.

Because of the marker arrangement pattern presenting means A6, this embodiment can present the user with an appropriate marker attaching method. The provision of the marker arrangement pattern selection means A8 allows the user to select an appropriate marker attaching method easily.

While in this embodiment we have shown an example case in which the CT apparatus has both the marker arrangement pattern presenting means A6 and the marker arrangement pattern selection means A8, the CT apparatus may have only one of them if it has a means for specifying a marker arrangement pattern.

Figure 5:
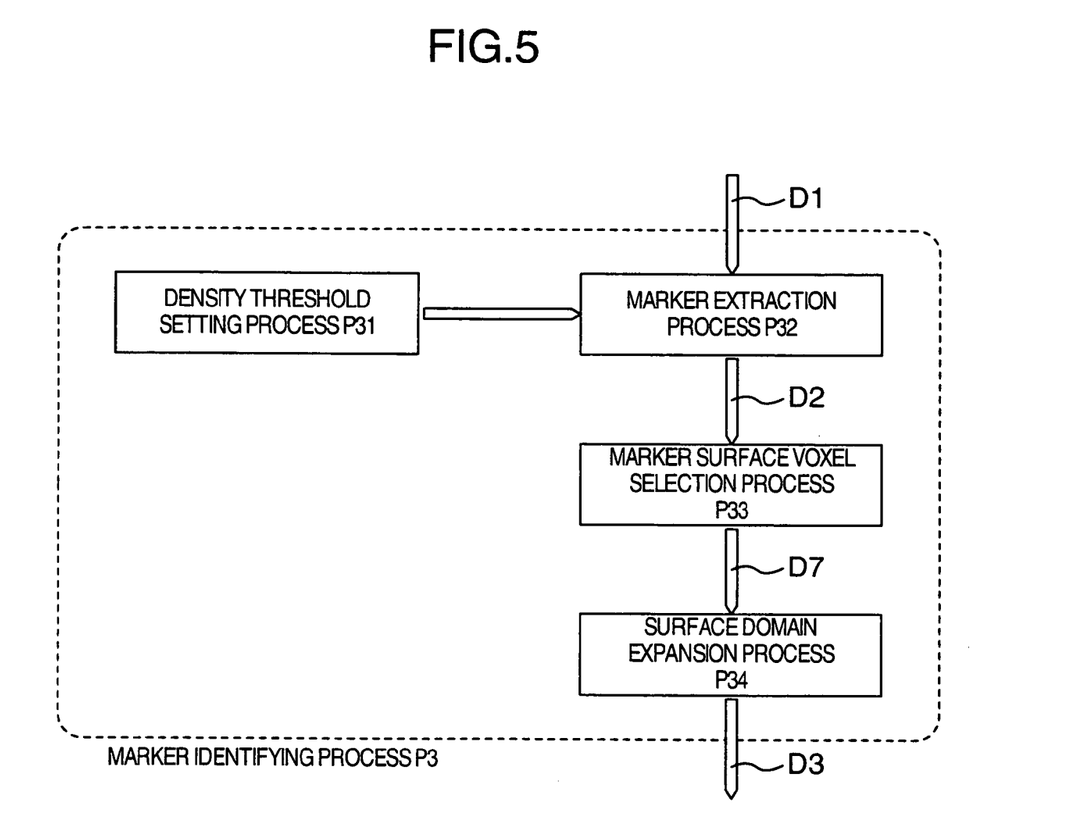
FIG. 5 is an explanatory diagram showing a marker identifying process P3 of FIG. 1.

Next, details of the marker identifying process P3 will be explained by referring to FIG. 5. The marker identifying process P3 includes a density threshold setting process P31, a marker extraction process P32, a marker surface voxel selection process P33, and a surface domain expansion process P34.

The density threshold setting process P31 is a process to set appropriate upper and lower thresholds for the marker density value. For example, when a plastic clay marker is to be attached to an aluminum object to be imaged, a threshold for lower limit is set at 1.0 g/cm$^3$ and an threshold for an upper limit is set at 2.0 g/cm$^3$, taking into account the fact that the clay density is about 1.5 g/cm$^3$.

The marker extraction process P32 is a process which involves making comparison, for all the voxels making up the coarse tomographic image set D1, between a material density described by the voxels and the threshold set by the density threshold setting process P31 and then extracting only those voxels corresponding to the markers. The voxel is a unit that makes up three-dimensional bit-map data.

In the above example, when the densities described in the voxels are higher than the upper threshold of 2.0 g/cm$^3$, they are replaced with 0 g/cm$^3$. This can eliminate the aluminum portion (voxels) from the coarse tomographic image set D1, leaving only the marker portion (voxels) in the set. This process produces a marker tomographic image set D2.

The marker surface voxel selection process P33 is a process to pick up some voxels from those on the surface of the marker. First, this process randomly extracts voxels making up the marker tomographic image set D2 and checks whether the extracted voxels are on the marker surface or not. If the extracted voxels are on the surface of the marker, these voxels are added to a voxel list D7. Here, several tens or several thousands of voxels are picked up.

The surface domain expansion process P34 assumes that a part of the marker surface has a geometric feature, and expands a feature surface domain by taking one voxel included in that part as a starting point, extracts a domain satisfying the geometric feature, and determines the geometric feature. This processing is performed by using the surface domain expansion method. The surface domain expansion method can extract domains with geometric features (geometric definitions), such as a part of flat surface, a part of cylindrical surface, a part of spherical surface, a part of revolution surface, a part of quadratic surface, and a part of translated surface.

Since the voxels on the marker surface are already extracted in the marker surface voxel selection process P33, these may be used as starting points. With the surface domain expansion method, it is necessary to determine beforehand which of the geometric features described above the domains containing the voxels of concern have, or to determine if these domains do not have such geometric features at all.

For this purpose, the surface domain expansion process P34 first assumes that a certain domain is a part of a planar surface and checks if this assumption is correct or not. This is done, for example, by attempting to extract a parameter defining the planar surface by the surface domain expansion method and then checking whether or not the parameter extraction is successfully completed. If it is found that the domain is not a part of the planar surface, another assumption is made that the domain is a part of a cylindrical surface and then a similar check is made to see if this assumption is correct. In this way, by successively repeating the process of making an assumption and checking the validity of this assumption, it is possible to determine what geometric feature a domain including the voxels of concern has.

Here, referring to FIG. 6A to FIG. 6D, one example process of extracting a geometric feature using the surface domain expansion method will be explained. In this example, a certain domain is assumed to be a "planar surface with an unknown normal." First, the coarse tomographic image set (three-dimensional bit-map data) D1 is transformed into point data D1$a$. An example transformation performed by a method that determines centers of two adjoining cells with a marker surface therebetween is shown in FIGS. 6A–6D. FIGS. 6A–6D is a partially enlarged view of the coarse tomographic image set D1, with cells (voxels) outside the marker shown blank and cells inside the marker shown hatched. Blank and black circles (○ and ●) at the cell boundaries correspond to the point data D1$a$.

Figure 6A:
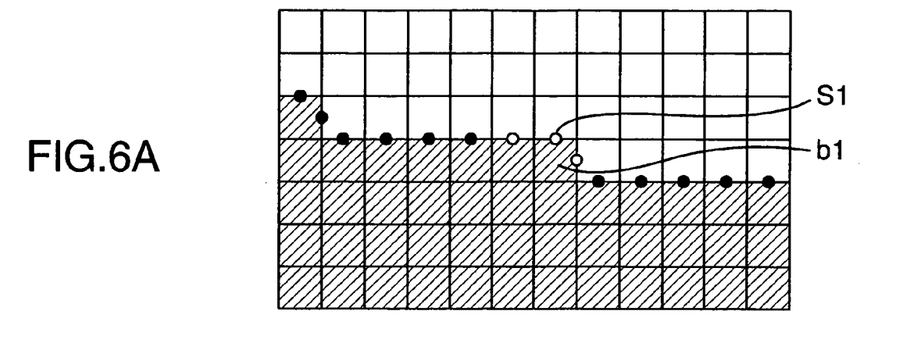
FIGS. 6A–6D are explanatory diagrams showing an example of how geometric features are extracted by the surface domain expansion method, FIG. 6A representing a group addition process, FIG. 6B a group boundary determination process, FIG. 6C a group expansion process, and FIG. 6D a state in which a group representative surface and boundaries are recalculated by the group boundary determination process.

In this example, a group of point data D1$a$ belonging to the "planar surface with an unknown normal" is determined and then a surface that best represents a set of points included in this group (representative surface) is determined. First, a group addition process starts the following processing by focusing on one cell. In the case of FIG. 6A, a cell b1 is the one under consideration. A blank circle on the boundary of the cell b1 is taken as a starting point S1, and two points adjoining S1 are added to the group to expand the group. A state in which the group has been expanded to three points is shown in FIG. 6A. In FIGS. 6A–6D, points belonging to the group are shown by "○" and those not belonging to the group by "●".

Figure 6B:
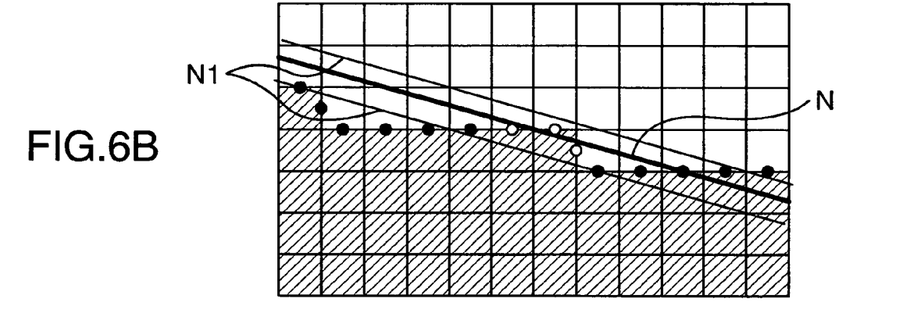

Next, a group boundary determination process determines a representative surface that best approximates a set of points belonging to the group by using the method of least squares. The representative surface is then offset toward the front and back (vertically up and down in FIG. 6B) to determine a boundary of the group. The amount of offset is 0.5–0.75 times a width of the cell. FIG. 6B shows a representative surface of the group indicated by a thick line N and its boundaries by thin lines N1.

Figure 6C:
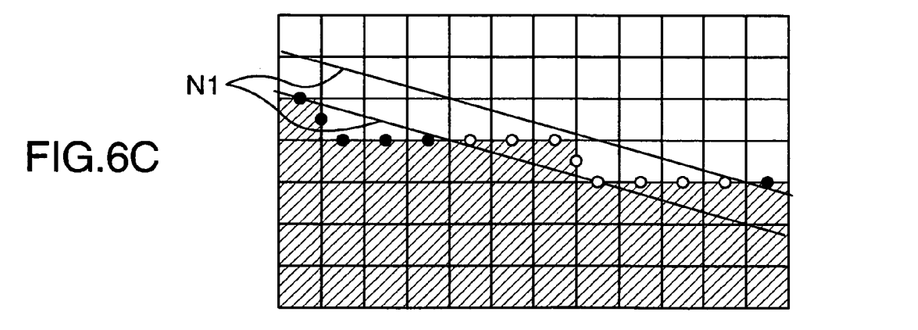

Next, a group expansion process adds new points to the group based on the group boundaries N1. More specifically, from among points not belonging to the group, those points adjoining the group are chosen and their coordinates are checked against the group boundaries N1. If there is any points positioned inside the boundaries N1, these points are added to the group. FIG. 6C shows an expanded state of the group after new points have been added to the group based on the boundaries N1.

Figure 6D:
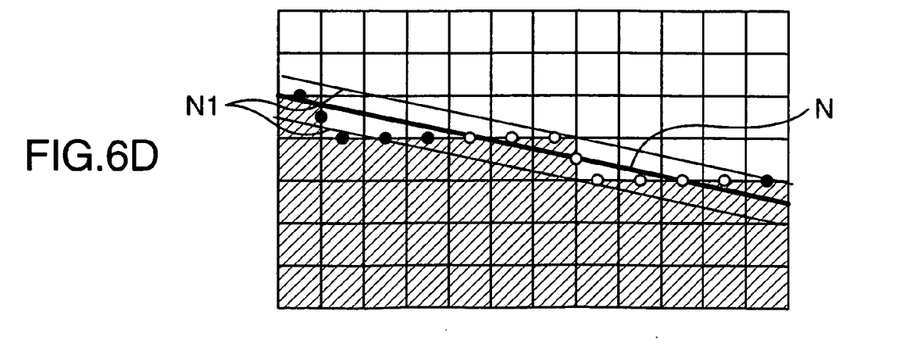

After new points have been added by the group expansion process, the processing returns to the group boundary determination process where it recalculates the representative surface and the boundaries of the group that have changed because of the addition of new points. FIG. 6D shows a recalculated representative surface N and boundaries N1 of the group. The group boundary determination process and the group expansion process are repeated until new points are no longer added to the group.

When the points belonging to the group no longer change, a reference point and a normal of the representative surface obtained at that point in time constitute a geometric feature of this group. The reference point of the representative surface may, for example, be a point among a set of points belonging to the group that is situated at the center. This reference point and the normal are parameters defining the planar surface.

In determining the representative surface in the group boundary determination process, if a residual obtained as a result of the minimum square method fails to converge to a sufficiently small value, the assumption that the domain under consideration is a part of a planar surface is not valid. This is equivalent to a parameter extraction failure.

Also for other point data D1$a$ on the marker surface, the group and its representative surface are calculated in the similar manner to clarify the contact surface between the marker and the object.

Described above is an example of how a geometric feature of the "planar surface with an unknown normal" is determined by the surface domain expansion method. The surface domain expansion method can determine a geometric feature according to a kind of the domain under consideration in a similar manner described above.

For example, as a geometric feature of a "cylindrical surface with an unknown radius," a reference point, axis and radius are determined. For a "spherical surface with an unknown radius" a center and a radius are determined as its geometric feature. For a "quadratic surface" coefficients of a quadratic equation with X, Y and Z as unknowns are determined as its geometric feature. For a "revolution surface" a reference point of a rotating axis, a reference vector and a line being revolved are determined as its geometric feature. For a "translated surface" a translated vector and line are determined as its geometric feature. These geometric features also constitute information representing a geometry of the contact surface between the marker and the object.

The surface domain expansion process P34 produces a marker surface feature domain list D3, a list of domains on the marker surface having geometric features. The marker surface feature domain list D3 lists up domains of the marker surface that are larger than a predetermined area and which have certain geometric features. Of the domains on the marker surface, those not in contact with the object are generally free curved surfaces not classified into any of the planar surface, cylindrical surface, spherical surface, revolution surface and translated surface, and therefore are not recorded in the marker surface feature domain list D3.

Figure 7:
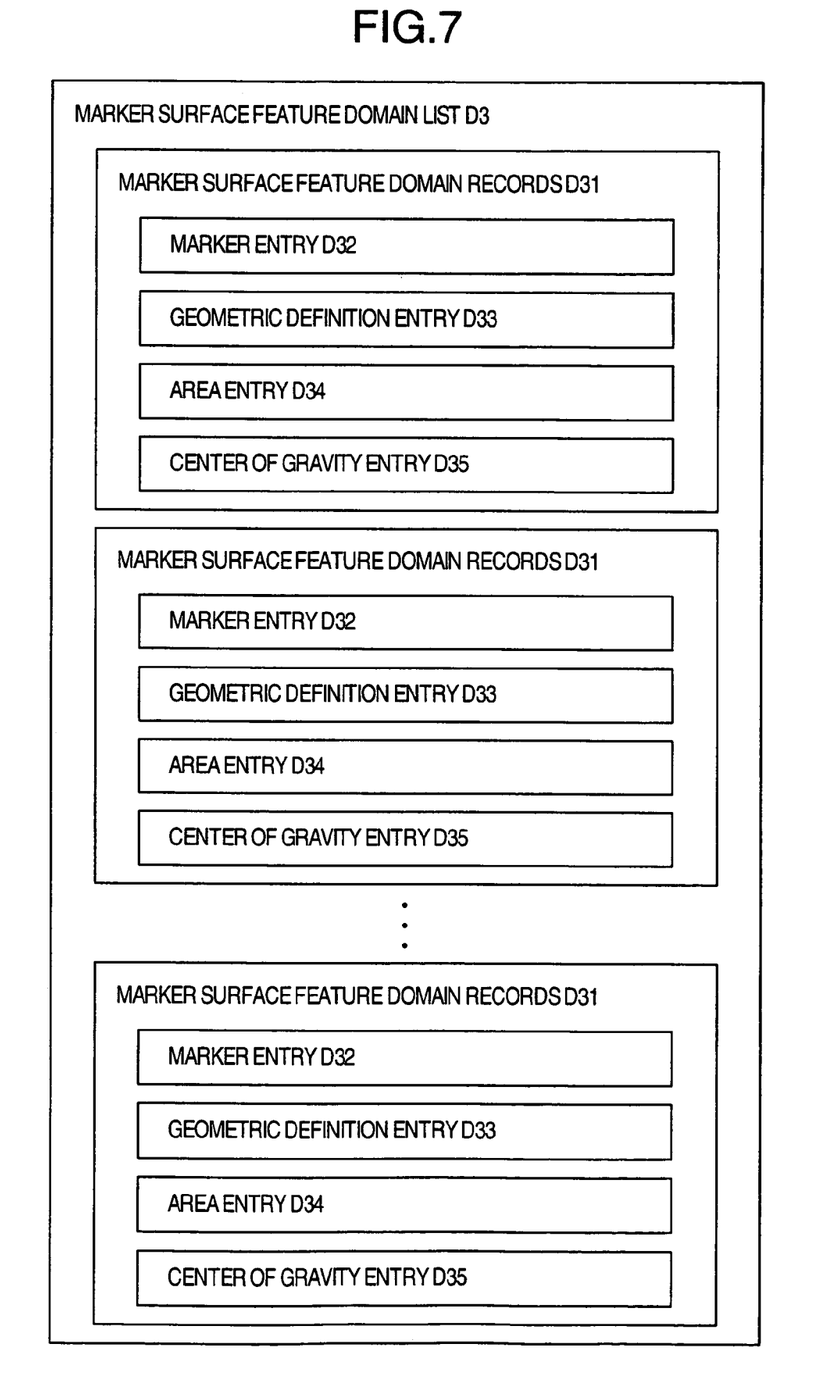
FIG. 7 is a diagram showing a typical example of a marker surface feature domain list D3.

A typical example of the marker surface feature domain list D3 is shown in FIG. 7. The marker surface feature domain list D3 is a set of marker surface feature domain records D31 describing individual domains having geometric features. The individual marker surface feature domain records D31 have a marker entry D32, a geometric definition entry D33, an area entry D34, and a center of gravity entry D35. These entries describe a marker to which the domain of concern belongs, a geometric definition of the domain, an area of the domain and a gravity center of the domain, respectively. The content of the entry is calculated by the surface domain expansion process P34 and recorded in the corresponding entry.

Figure 8:
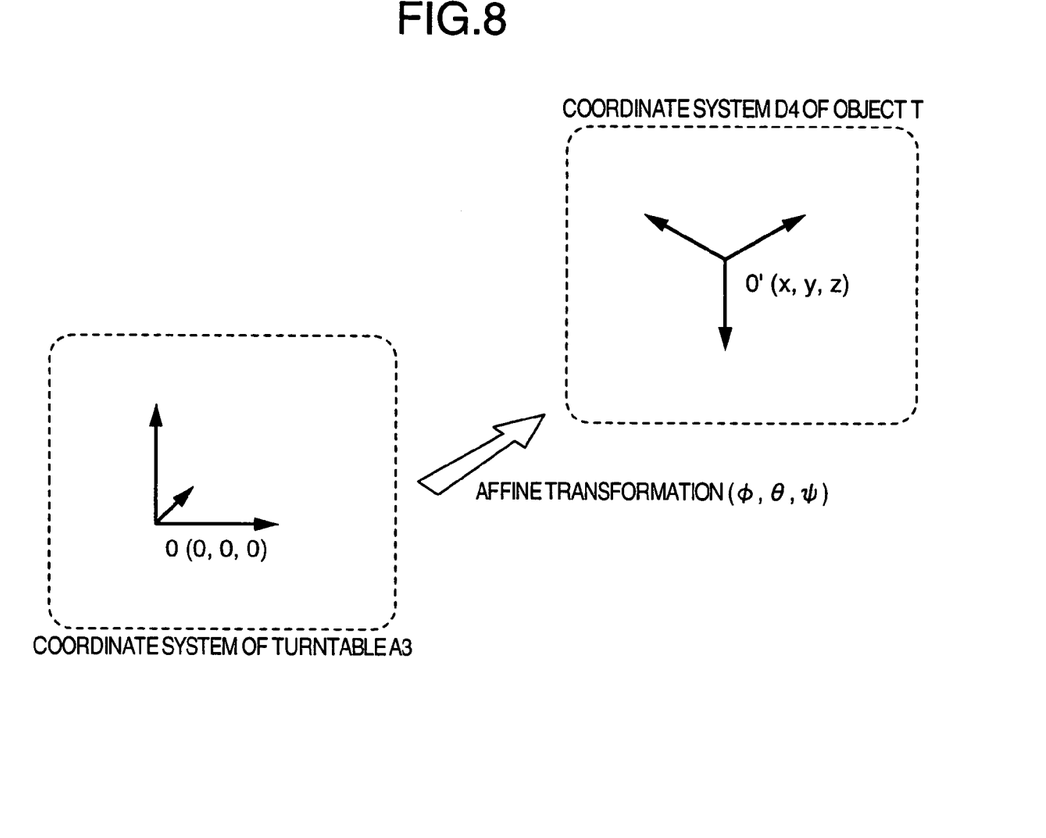
FIG. 8 is an explanatory diagram showing a coordinate system determination process P4 of FIG. 1.

Next, details of the coordinate system determination process P4 will be explained by referring to FIG. 8. A three-dimensional Cartesian coordinate system can be defined by determining a reference point and three orthogonal reference axes. For this purpose six parameters need to be specified. These six parameters are expressed as (x, y, z, $\phi$, $\theta$, $\psi$). Of these, (x, y, z) are parameters for determining a position of the reference point, and ($\phi$, $\theta$, $\psi$) are parameters for determining an affine transformation matrix that specifies directions of the three reference axes. ($\phi$, $\theta$, $\psi$) are generally known as an Eulerian angle.

The coordinate system determination process P4 determines six parameters from the marker surface feature domain list D3 according to the marker arrangement pattern the user has selected using the marker arrangement pattern selection means A8. For example, in the case of the marker arrangement pattern shown in FIG. 2A, an intersecting point of the three planes recorded in the marker surface feature domain list D3 is taken as a reference point and, based on the coordinates of the reference point, the parameters (x, y, z) are determined. The parameters ($\phi$, $\theta$, $\psi$) are determined by using a multidimensional convergence calculation technique, called a valley descending technique or hill climbing technique. For example, they can be determined such that a value of an evaluation function shown in Equation 1 is minimum.

[Equation 1]

$$f(\phi, \theta, \psi) = \text{Min} \begin{Bmatrix} (LAX')^2 + (LBY')^2 + (LCZ')^2, \\ (LAX')^2 + (LBZ')^2 + (LCY')^2, \\ (LAY')^2 + (LBX')^2 + (LCZ')^2, \\ (LAY')^2 + (LBZ')^2 + (LCX')^2, \\ (LAZ')^2 + (LBX')^2 + (LCY')^2, \\ (LAZ')^2 + (LBY')^2 + (LCX')^2, \end{Bmatrix} \quad \text{(Equation 1)}$$

In Equation 1, A, B and C represent three planes recorded in the marker surface feature domain list D3. X', Y' and Z' represent three planes that are obtained through transforming the three reference planes (XY plane, YZ plane, ZX plane) preset with respect to the turntable A3 of the X-ray CT apparatus by an affine transformation matrix determined by the parameters ($\phi$, $\theta$, $\psi$). Z represents an angle between the intersecting planes.

In this embodiment, a prespecified reference plane of an object is extracted by a CT image and then, based on a positional relation between this reference plane and the coordinate system of the turntable of the CT apparatus, a tomographic image of a prespecified portion is obtained.

In the first embodiment described above, even if objects with is different reference planes are set on the turntable for imaging, the user can omit the step of determining reference planes of each object, facilitating the placement of the objects and the operation of the X-ray CT apparatus.

In this embodiment an example case has been described in which the marker density is smaller than that of the object. Considering an attenuation of X-rays by the marker, this configuration is preferred. But if the density of the maker is larger than that of the object, this embodiment is still effective in omitting the work of determining the reference planes of the object.

Second Embodiment

In the first embodiment, we have described a case where plastic clay markers are directly attached to an object. A second embodiment concerns a case where markers are attached to an object through a pad. The pad has a small thickness compared with its size (length and width) and is made of a material with a smaller density than that of the marker.

Figure 9:
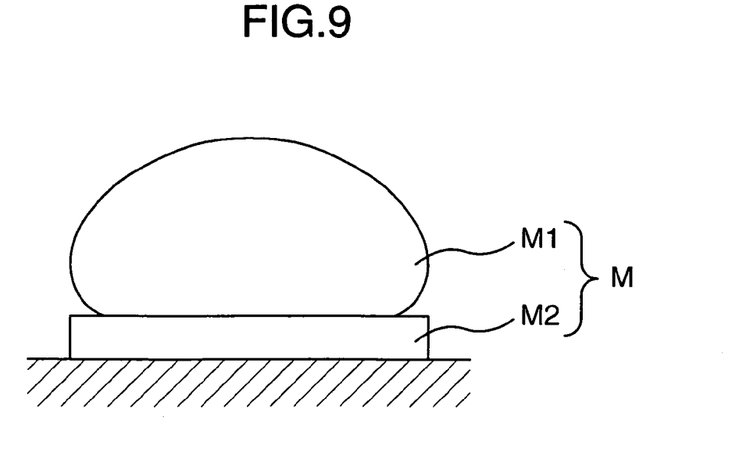
FIG. 9 is a schematic diagram of a second embodiment of the invention showing a marker attached to an object.

How the marker is attached to an object in this embodiment is shown in FIG. 9. The marker M includes a marker body M1 and a marker pad M2. The marker body M1 is made of a plastic clay with a density of about 1.5 g/cm$^3$ and a size of 20–50 mm. The marker pad M2 is made of a light and deformable material such as foamed urethane, and is about 2 mm thick.

The marker pad M2 has so small a density of about 0.1 g/cm$^3$ that it does not show up in a tomogram output from the X-ray CT apparatus. Thus, on the tomographic image set, the object T and the marker body M1 are completely separated, facilitating the subsequent image processing to a great extent. To prevent the marker pad M2 from being imaged in the tomogram, the density of the marker pad M2 need only be 20% or less of the density of the object T.

Figure 10:
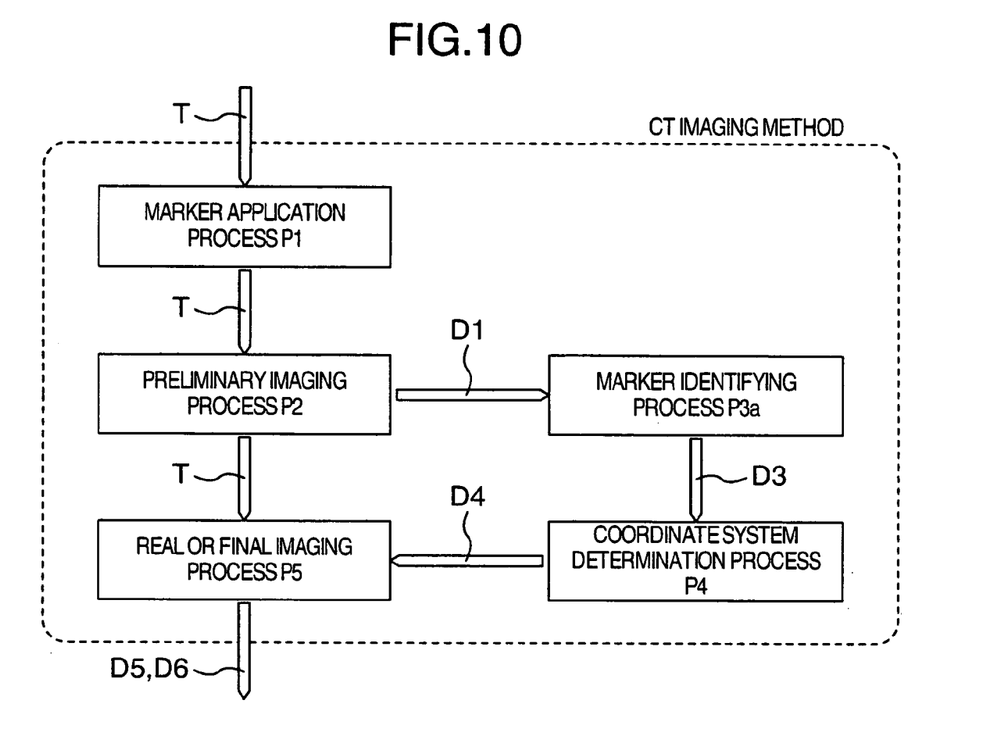
FIG. 10 is a diagram showing the second embodiment concerning a CT imaging method of the invention.

The second embodiment of the CT imaging method using the marker body M1 and the marker pad M2 of FIG. 9 is shown in FIG. 10. A point in which this CT imaging method differs from the first embodiment of FIG. 1 is that this method includes a marker identifying process P3a instead of the marker identifying process P3. Other processes are the same as in FIG. 1 and are not described here.

Figure 11:
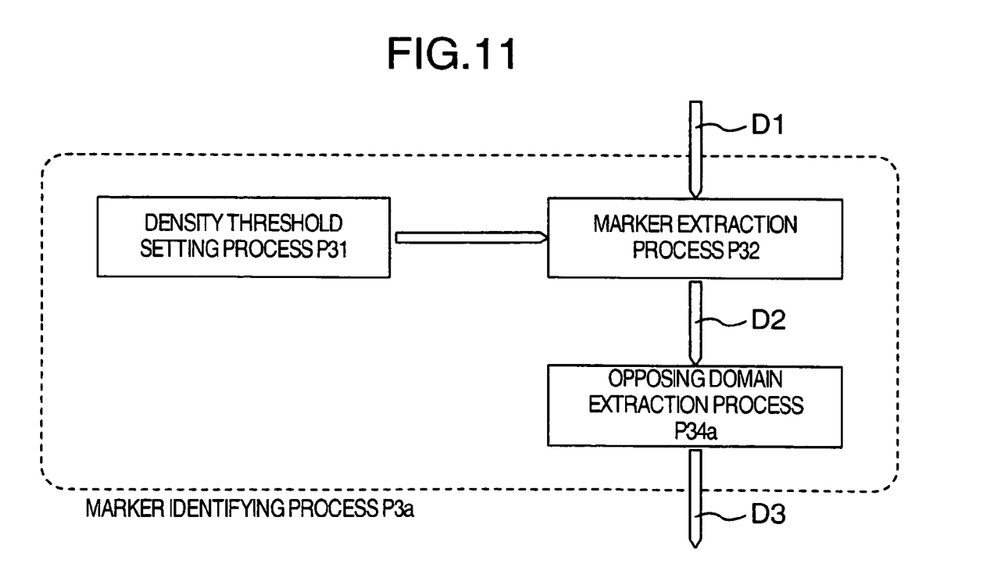
FIG. 11 is an explanatory diagram of a marker identifying process P3a of FIG. 10.

Details of the marker identifying process P3a will be explained by referring to FIG. 11. What is different from the marker identifying process P3 of FIG. 5 is that the marker identifying process P3a includes an opposing domain extraction process P34a instead of the marker surface voxel selection process P33 and the surface domain expansion process P34. Other processes are the same as those of FIG. 5 and are not described here.

The opposing domain extraction process P34a first extracts domains of the surface of the marker body M1 whose distances from the surface of the object T are almost equal to the thickness of the marker pad M2. Next, domains of the surface of the object T that oppose the extracted surface domains of the marker body M1 with the marker pad M2 interposed therebetween are determined. Based on the surface domains of the object T thus determined, the marker surface feature domain list D3, a list of domains having geometric features, is prepared. This processing can be performed, as in the surface domain expansion process P34 of FIG. 5, by successively checking whether or not the hypothesis that the domain of concern has a certain geometric feature is valid.

As in the first embodiment, when objects with different reference planes are set on the turntable for imaging, this embodiment also allows the user to omit the step of determining the reference planes of the objects, facilitating the placement of the objects and the operation of the X-ray CT apparatus.

Third Embodiment

Figure 12:
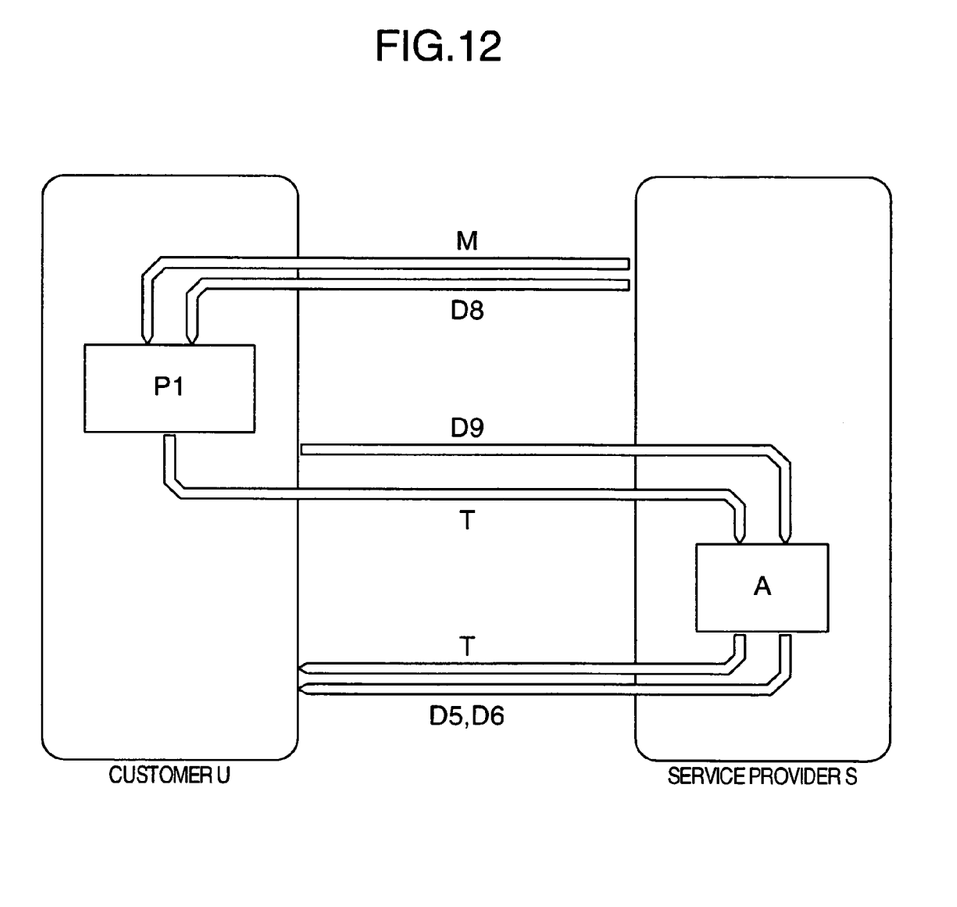
FIG. 12 is a schematic diagram showing a third embodiment of the invention concerning a CT imaging service method.

A third embodiment of the present invention concerning a CT imaging service method using the CT imaging method is shown in FIG. 12. This CT imaging service is for a service provider S to take tomographic images of an object T owned by a customer U by using an X-ray CT apparatus A and then provide the customer U with obtained tomographic images D5 and/or a tomographic image set D6. With this embodiment, the use of the method shown in FIG. 1 or FIG. 10 can not only simplify the tomographic imaging process but provide the CT imaging service also for objects that require a high level of confidentiality.

In this CT imaging service, a business transaction is initiated by a customer U applying to the service provider S for the service. Upon receipt of an application from the customer, the service provider S issues an instruction D8 to the customer U and sends a marker M or a plastic clay, the material of the marker, to the customer. The instruction D8 is a documentation that describes how to attach the maker M to an object T. The instruction D8 illustrates multiple marker arrangement patterns as shown in FIG. 2.

The customer U chooses an appropriate marker arrangement pattern from those illustrated in the instruction D8 and, according to the chosen pattern, attaches the marker M to the reference surfaces of the object T. That is, the customer U executes the marker application process P1 shown in FIG. 1 and FIG. 10.

After having attached all the necessary markers M to the object T, the customer U packs it in a shock-absorbing material, puts it in a container and sends it to the service provider S. At this time, the customer U prepares an instruction D9 specifying portions to be imaged and sends it along with the object T to the service provider S. The imaging instruction D9 includes information specifying the marker arrangement pattern selected by the customer U and information for specifying portions of the object the customer U wants to image.

The service provider S receives a container with the object T in it and fixes the container as is on the turntable A3 of the X-ray CT apparatus A. The container may be hermetically closed or sealed so that the object T may not be seen from outside.

Next, the service provider S, according to the imaging instruction D9 from the customer U, enters information on the portions to be imaged into the X-ray CT apparatus A. The marker arrangement pattern specified in the instruction D9 is also entered into the X-ray CT apparatus A by the marker arrangement pattern selection means A8. With these preparations completed, the image by the X-ray CT apparatus A is started.

The X-ray CT apparatus automatically executes all the processes, i.e., the preliminary imaging process P2, marker identifying process P3 or P3a, coordinate system determination process P4 and real or final imaging process P5. After the X-ray CT apparatus A has output the tomographic images D5 and/or tomographic image set D6 and their contents have been confirmed, the service provider S takes the container off the turntable A3 and returns it to the customer. The tomographic images D5 and/or tomographic image set D6 produced by the image operation are also returned to the customer U and a service fee is charged to the customer. The tomographic images D5 and/or tomographic image set D6 to be sent to the customer U are specified by the customer U at time of application.

This embodiment extracts by the CT image the reference planes of an object specified by the customer U and, based on a relation between the reference planes and the coordinate system of the turntable of the CT apparatus, produces tomographic images of a portion specified by the customer U.

In this CT imaging service, the object is returned in the same state as it was placed in the container by the customer. Thus, should a third party open the container and take the object during transport or storage, the customer U can easily detect an anomaly and take necessary actions appropriately. Further, if the container is sealed, the container cannot be opened by a third party without being readily noticed. This is suited to a CT imaging service for those objects that require high levels of confidentiality. Further, if the object has a complex shape, there is no need to manufacture a special jig for fixing the object at an appropriate angle, making it easier for the customer U to use the service.

On the side of the service provider S, this service method saves the service provider the labor of picking up an object from the container and putting it again in the container. Further, this service method can eliminate a troublesome work of determining reference planes of the object required to align the angle of the object to the turntable. Therefore, the placement of the object and the operation of the X-ray CT apparatus are made easier, reducing the delivery period and service cost of the CT imaging service.

In this embodiment an example case has been described in which a customer U prepares a container to accommodate an object. It is also possible for the service provider S to send the container and shock-absorbing material to the customer U. In that case, the service provider S selects an appropriate size of the container and an appropriate material (density) of the shock-absorbing material according to information on the size and material (density) of an object obtained from the customer U. This permits the service provider S to efficiently execute the imaging of the object using the X-ray CT apparatus.

The container suitably has a high X-ray transmissivity, a low X-ray attenuation rate, and a low density. More specifically, paper, corrugated cardboard, wood, plastics and resin may be used as container materials. A low density metal may also be used.

In the above embodiments, we have described a CT apparatus using X-rays. It is also possible to apply the present invention to CT apparatuses using other radiations ($\alpha$, $\beta$ and $\gamma$ rays) and still produce the similar effects or advantages. In that case, the only requirement is to use a marker of a material with a different radiation transmissivity (or attenuation rate) from that of an object to be imaged.

With this invention, even when objects with different reference planes are to be set on the turntable for CT imaging, the user can omit the step of determining the reference planes of the objects and thus facilitate the placement of the objects.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A CT imaging method comprising the steps of:
   imaging an object to be imaged by a CT apparatus using an X-ray or radiation, and obtaining a tomographic image thereof, said object including a reference portion;

processing said tomographic image and obtaining a relative positional relation between a reference coordinate system of said object and a coordinate system of the CT apparatus; and imaging said object by the CT apparatus, and based on said relative positional relation, obtaining a tomographic image of a desired position of said object.

2. A CT imaging method comprising the steps of:

imaging an object to be imaged by a CT apparatus using an X-ray or radiation and obtaining a tomographic image thereof, said object including a reference portion;

obtaining geometric features of a reference surface of said reference portion from said tomogrpahic image, and based on said geometric features, obtaining a relative positional relation between a reference coordinate system of said object and a coordinate system of the CT apparatus; and imaging said object by the CT apparatus, and based on said relative positional relation, obtaining a tomographic image of a desired portion of said object.

3. A CT imaging method of imaging an object to be imaged, said object being placed on a turntable capable of rotating and translating said object, comprising the steps of:

imaging an object to be imaged by a CT apparatus using an X-ray or radiation and obtaining a tomographic image thereof, said object including a reference portion;

processing said tomographic image and obtaining a relative positional relation between a reference coordinate system of said object and a coordinate system of said turntable of the CT apparatus; and imaging said object by the CT apparatus, and based on said relative positional relation, obtaining a tomographic image of a desired portion of said object.

4. A CT apparatus for imaging an object to be imaged using an X-ray or radiation, said object including a reference portion, comprising:

means for obtaining a tomographic image of said object including said reference portion;

means for processing said tomographic image and obtaining a relative positional relation between a reference coordinate system of said object and a coordinate system of the CT apparatus; and means for imaging said object, and based on said relative positional relation, obtaining a tomographic image of a desired portion of said object.

5. A CT apparatus for imaging an object to be imaged using an X-ray or radiation, said object including a reference portion, comprising:

means for obtaining a tomographic image of said object including said reference portion;

means for obtaining geometric features of a reference surface of said reference portion from said tomographic image, and based on said geometric features, obtaining a relative positional relation between a reference coordinate system of said object and a coordinate system of the CT apparatus; and means for imaging said object, and based on said relative positional relation, obtaining a tomographic image of a desired portion of said object.

6. A CT apparatus for imaging an object to be imaged, said object being placed on a turntable capable of rotating and translating said object, comprising:

means for imaging said object including a reference portion using an X-ray or radiation and obtaining a tomographic image thereof;

means for processing said tomographic image and obtaining a relative positional relation between a reference coordinate system of said object and a coordinate system of said turntable of the CT apparatus; and means for imaging said object, and based on said relative positional relation, obtaining a tomographic image of a desired portion of said object.

* * * * *